United States Patent [19]

Liu et al.

[11] Patent Number: 4,650,770
[45] Date of Patent: Mar. 17, 1987

[54] ENERGY ABSORBING PARTICLE QUENCHING IN LIGHT EMITTING COMPETITIVE PROTEIN BINDING ASSAYS

[75] Inventors: Yen-Ping Liu, Santa Clara; Edwin F. Ullman, Atherton; Martin J. Becker, Palo Alto, all of Calif.

[73] Assignee: Syntex (U.S.A.) Inc., Palo Alto, Calif.

[21] Appl. No.: 559,555

[22] Filed: Dec. 7, 1983

Related U.S. Application Data

[63] Continuation of Ser. No. 258,176, Apr. 27, 1981, abandoned.

[51] Int. Cl.$^4$ .................. G01N 33/543; G01N 33/546; G01N 33/542; G01N 33/533
[52] U.S. Cl. .................... 436/523; 436/533; 436/534; 436/537; 436/546; 436/805
[58] Field of Search .............. 436/518, 524, 528, 533, 436/534, 537, 546, 523; 424/7.1

[56] References Cited

U.S. PATENT DOCUMENTS

| | | | |
|---|---|---|---|
| 3,853,987 | 12/1974 | Dreyer | 424/12 X |
| 4,199,559 | 4/1980 | Ullman | 424/8 |
| 4,208,479 | 6/1980 | Zuk | 23/230 B |
| 4,275,149 | 6/1981 | Litman | 435/7 |
| 4,318,707 | 3/1982 | Litman | 23/230 B |
| 4,407,964 | 10/1983 | Elings | 436/533 X |

Primary Examiner—Esther M. Kepplinger
Assistant Examiner—Jeremy Jay
Attorney, Agent, or Firm—Theodore J. Leitereg; Bertram I. Rowland

[57] ABSTRACT

Assays are provided employing particles and absorbent particles, wherein the absorbent particles substantially inhibit fluorescence when bound to the fluorescent particles through specific non-covalent binding.

14 Claims, No Drawings

ENERGY ABSORBING PARTICLE QUENCHING IN LIGHT EMITTING COMPETITIVE PROTEIN BINDING ASSAYS

This is a continuation of copending application U.S. Ser. No. 258,176, filed Apr. 27, 1981, now abandoned.

BACKGROUND OF THE INVENTION

1. Field of the Invention

There have been increasing efforts to develop convenient and sensitive techniques for determining either qualitatively or quantitatively a wide variety of compounds of interest, either physiological or non-physiological. Many of the compounds are haptenic, frequently drugs, and are monitored in the treatment of mammals. Other compounds are naturally occurring compounds which are used for the diagnosis of dysfunctions such as auto antibodies and surface antigens on neoplastic cells. Other assays are concerned with the presence of microorganisms, particularly as evidenced by a distinctive surface antigen.

Depending upon the nature of the analyte and its source, the nature of the assay can be affected. Where the analyte cannot be obtained in pure form, labeling of an impure mixture of the analyte can result in a substantial amount of background signal. For the most part, other than monoclonal antibodies, antiserum is a complex mixture of antibodies. Again, labeling of a heterogeneous antiserum can also result in a large background signal. Other considerations involve interference from materials naturally occurring in the sample, manipulative convenience, sensitivity to variations in concentration in the range of interest of the analyte, available instrumentation and the like.

As the need has increased for increasing sensitivity and dependability, new protocols employing new reagents have been sought. Each new improvement has been only difficultly achieved in the light of past experience. Means for amplifying the signal resulting from the presence of analyte has been one approach to provide greater sensitivity. Many of these assays have depended upon enzymes or fluorescers because of many advantages which they afford. With fluorescers, it is desirable to be able to modulate a large number of fluorescer molecules in relation to each molecule of analyte.

2. Description of the Prior Art

U.S. patent application Ser. No. 28,640, now U.S. Pat. No. 4,256,834, filed Apr. 9, 1979, discloses the use of charcoal as a scavenger particle in competitive protein binding assays. U.S. Pat. No. 3,853,987 describes fluorescent particles in a competitive protein binding assay. U.S. Pat. No. 3,900,558 describes the uptake of fluorescent molecules by mast cells in an assay. U.S. Pat. No. 4,061,466 describes the use of gel particles for entrapping reagents in assays. U.S. Pat. No. 4,102,990 describes the use of particles of different electrophoretic properties, which are bound together by specific binding complexes in an assay. U.S. Pat. No. 4,138,213 describes the use of rheumatoid factor and Clq for particle agglutination in an assay. Application Ser. No. 964,099 now U.S. Pat. No. 4,275,149, at page 68, teaches charcoal as a quencher inhibited from entering a fluorescein containing particle.

SUMMARY OF THE INVENTION

Methods of measuring analytes are taught employing functionalized fluorescent particles and functionalized energy absorbent particles capable of quenching a substantial portion of the fluorescent signal, when in close proximity to the fluorescent particle due to specific non-covalent binding. Particularly, members of binding pairs are bound to fluorescent particles and absorbent particles to provide reagents for the determination of an analyte, which is also a member of a specific binding pair. When the functionalized particles are brought together in an assay medium in the presence of analyte, the number of energy absorbent particles brought into close juxtaposition to the fluorescent particles is related to the amount of analyte in the medium. The presence of the energy absorbent particle adjacent the fluorescent particle results in a substantial diminution of the fluorescence from the fluorescent particle, so that the observed fluorescent signal is greater changed in relation to small changes in the amount of analyte in the medium.

DESCRIPTION OF THE SPECIFIC EMBODIMENTS

A simple, sensitive and accurate method is provided for determining low concentrations of a wide variety of organic materials. The materials include those having physiological activity, such as drugs, synthetic or naturally occurring, disease related materials including cells and viruses, as well as other materials, such as contaminants, pollutants, chemical processing impurities and the like. The subject method is of the category referred to as "homogeneous" assays in that it does not require a separation step between mip-bound label bound to the complementary mip and mip-bound-label which is unbound and free to diffuse in the solution. (Mip will be defined subsequently). The subject invention provides for a high level of multiplication in that a substantial change in signal can be observed at extremely small differences in concentration of the analyte.

The method also affords substantial advantages when concerned with impure mixtures of specific binding pair members. In many instances, the analyte of interest and/or its specific binding partner or receptor may be present in less than about 50% of the mixture. Frequently, purification is difficult and sometimes impossible, so that one must deal with the impure mixture. In many assays, it is necessary to label either the analyte or the receptor, with the result that much of the label may be present on components other than members of the specific binding pair. The presence of the contaminating label in the assay medium results in a background signal which is not subject to modulation, but may be subject to non-specific effects. The background signal can result in substantial errors in the determination of the analyte, reduce the response to variations in concentration of the analyte and enhance the incidence of erroneous results.

In the subject invention, the above problems are either alleviated or cured by providing for dispersible particulate reagents to which a plurality of members of the specific binding pair may be bound and which provide for substantial modulation of the signal when the reagents are bound together by binding of specific binding partners.

The first reagent is a fluorescent particle to which a member of the specific binding pair is bound, either covalently or non-covalently. By binding a plurality of molecules from an impure mixture of the specific binding member, there is a substantially high probability that at least one specific binding pair member will be bound to each one of the particles present in the reaction medium. The second reagent is a quenching particle to which is bound a member of a specific binding pair which member provides for binding of the quenching particle to the fluorescent particle in proportion to the amount of analyte present in the medium. Depending upon the nature of the analyte, the binding of the quenching particle to the fluorescent particle can be inhibited by the analyte or effected by the analyte binding to the fluorescent particle or quenching particle.

Both the fluorescent particle conjugate and the quenching conjugate are discrete insoluble particles. The nature of the particles is chosen so that they can be readily disposed in the assay medium, retain their integrity, and will interact to modulate the fluorescent signal when bound together through bridging by the specific binding pair members and the linking groups, if any, by which the specific binding members are bound to the particles.

The analyte will be a member of a specific binding pair, consisting of ligand and its homologous receptor. At least one of the members of the specific binding pair involving the analyte will be bound, directly or indirectly, covalently or non-covalently, to at least one of the two particles. While normally, only members of the specific binding pair involving the analyte will be involved in binding to the particles, there are a number of situations, where other than a member of the specific binding pair of which the analyte is a member will be involved.

In carrying out the subject method, one combines in an appropriate assay medium, the analyte containing sample, the fluorescent particle conjugate, the energy absorbent or quenching particle conjugate, as well as any additional reagents and determines the fluorescent signal from the assay medium. By comparing the observed signal with the signal obtained from an assay medium having a known amount of analyte, one can qualitatively, semi-quantitatively or quantitatively determine the analyst of interest.

DEFINITIONS

Analyte—the compound or composition to be measured, which may be a ligand, which is mono- or polyepitopic, antigenic or haptenic, a single or plurality of compounds which share at least one common epitopic site; or a receptor.

Specific Binding Pair—two different molecules, where one of the molecules has an area on the surface or in a cavity which specifically binds to a particular spatial and polar organization of the other molecule or molecular complex involving the other molecules. For the most part, the members of the specific binding pair are referred to as ligand and receptor (anti-ligand); where a receptor only binds to a complex of two or more molecules, the ligand will be referred to as a complex and the receptor as anti-complex.

Ligand—any organic compound for which a receptor naturally exists or can be prepared.

Receptor (anti-ligand)—any compound or composition capable of recognizing a particular spatial and polar organization of a molecule, i.e., determinant or epitopic site. Illustrative of receptors include naturally occurring receptors, e.g. thyroxine binding globulin, antibodies, enzymes, Fab fragments, lectins and the like.

Complex—non-covalently bound aggregates of two or more molecules, usually comprised of a ligand and an anti-ligand.

Anti-Complex—a molecule capable of binding to a complex, such as comprised of a ligand anti-ligand, where the binding affinity of the anti-complex to the complex is substantially higher than to individual members of the complex.

Ligand Analog—a modified ligand which can compete with the analogous ligand for a receptor, the modification providing means for covalently joining the ligand analog to another molecule. The ligand analog will normally differ from the ligand by more than replacement of a hydrogen with a bond which links the ligand analog to a hub or molecule.

Fluorescent Particle—a solid insoluble particle of at least about 50 nm in diameter, readily dispersible in an aqueous medium, to which may be stably bound a member of a specific binding pair. For the most part, the solids will be non-porous relative to members of the specific binding pair, may have one or more layers, will be at least partially transparent to light at the emission range of the fluorescer and will have little if any electrostatic attraction for the energy absorbent particle. The particle will be fluorescent or phosphorescent when activated by electromagnetic radiation or chemically activated.

Energy absorbent or quenching particle—a solid insoluble particle of at least about 50 nm in diameter capable of quenching the fluorescence of the fluorescent particle when within the distance resulting from specific binding between members of specific binding pairs. The quenching particle may be the same or different, usually different, from the fluorescent particle. Normally, the quenching particle will provide a substantial quenching at a distance of more than about 50 Å, preferably more than about 500 Å, more preferably more than about 2000 Å, where the distance is measured from the surfaces of the particles.

Mip—While mip is an acronym for a member of an immunological pair, for the purposes of this invention, mip will be expanded beyond members of an immunological pair to include a member of any ligand and receptor pair, as well as complexes and anti-complexes.

METHOD

The subject assay is carried out in an aqueous zone at a moderate pH, generally close to optimum assay sensitivity, without separation of the assay components or products. The assay zone for the determination of analyte is prepared by employing an appropriate aqueous medium, normally buffered the unknown sample, which may have been subject to prior treatment, the fluorescent particle, the quenching particles, as well as members of the specific binding pair or their analogs, as required.

The presence of analyte—ligand or its homologous receptor (anti-ligand)—in the unknown sample will modulate the bridging between the fluorescent particle and the quanching particle that will bring the quenching particle within quenching distance of the fluorescent particle. In effect, the analyte affects the average distance between the quenching particle and the fluorescent particle in the assay medium, modulating the population of quenching particles within quenching distance of the fluorescent particles. Therefore, the observed signal will be related to the amount of analyte in the sample.

In carrying out the assay, an aqueous medium will normally be employed. Other polar solvents may also be included, usually oxygenated organic solvents of from 1 to 6, more usually from 1 to 4 carbon atoms, including alcohols, ethers and the like. Usually these cosolvents will be present in less than about 40 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the assay and usually constant temperatures during the period of the measurement, particularly for rate determinations. The temperatures for the determination will generally range from about 10°–50° C., more usually from about 15°–40° C.

The concentration of analyte which may be assayed will generally vary from about $10^{-4}$ to $10^{-5}$M, more usually from about $10^{-6}$ to $10^{-13}$M. Considerations such as whether the assay is qualitative, semi-quantitative or quantitative, the particular detection technique and the concentration of the analyte of interest will normally determine the concentration of the other reagents.

While the concentrations of the various reagents in the assay medium will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on analyte binding sites and usually not more than about 100,000 times the maximum concentration of interest based on analyte binding sites, usually about 0.1 to 1000 times, more usually about 0.3–100 times the maximum concentration of interest. By concentration is intended the available concentration, that is, the concentration at saturation, and not necessarily the actual concentration where members of the specific binding pair may not be equally available for binding.

The nature of the reagents and the protocols employed will affect the amount of each reagent whiich may be present. A serious limitation to the amount of the quenching particle in the assay medium, when the quenching particle is opaque in the absorption and/or emission band of the fluorescer, is the effect the opaque particle has on the amount of light which can be introduced into the assay medium, and the amount of light which can be emitted from the assay medium. Generally, the amount of opaque particle will result in a reduction of less than about 98%, preferably less than about 75% and more preferably less than about 40% of the available fluorescence from the fluorescent particles in the absence of any binding of the opaque particles to the fluorescent particles.

In situations where competitions are involved, usually there will be greater sensitivity when there is less than a stoichiometric amount of one reagent relative to the analyte. Where one reagent is first combined with the sample suspected of containing the analyte and the mixture allowed to go substantially to equilibrium, usually there will be a relatively small excess of the analyte, while an excess of the other reagent may not adversely affect the sensitivity of the assay. Because particles tend to diffuse only slowly in solution, there will normally be a trading off between the time for the assay and the amount of reagent employed in the assay.

Binding of the quenching particles to the fluorescent particle can be as a result of having a mip bound to one particle and the reciprocal mip bound to the other particle. By combining the analyte with the particle to which the reciprocal mip is conjugated, followed by the addition of the particle to which the analyte or its analog is conjugated, to the extent that available binding sites have been filled by the analyte, the binding of the two particles will be inhibited.

Binding of analyte to one of the particles may alternatively provide for the binding of the quanching particle to the fluorescent particle. Where the analyte is polyvalent, such as with antigens and antibodies, the analyte may act as a bridge, where the reciprocal mip is bound to the particles. Thus, where antibody is the analyte, by binding antigen to both fluorescent particles and quenching particles, the antibody may bridge antigen molecules bound to separate particles. This has the disadvantage, that the antibody cannot distinguish between the same particles and different particles, so that there can be joining of both fluorescent particles together and quenching particles together. The same situation applies where the analyte is an antigen, if the analyte is multivalent with respect to its homologous mip. It is therefore preferable to employ the first particle to be combined with the sample in less than a stoichiometric amount to avoid agglutination, and to employ the second particle in large stoichiometric excess.

An alternative technique is to have anti(antiligand) bound to one particle and ligand bound to the other particle. With antiligand as the analyte, one would combine the sample with the ligand conjugated particle in excess, followed by the addition of excess anti(antiligand) conjugated particle.

Where the anti(antiligand) binds to a single site of the antiligand e.g. protein-A or monoclonal antibodies, the antiligand analyte could be added to excess anti(antiligand) conjugated particle followed by the addition of ligand conjugated particle.

A further variation employs antiligands having specificities to different haptenic sites of an antigen, antiligand of one specificity conjugated to one type particle and the antiligand of the other specificity conjugated to the other type particle. The ligand should have only one of each of the haptenic sites. Any order of addition is permissible and both conjugates may be in excess. Where only one of the antiligands is specific for a single site, that antiligand conjugated particle will be added first. Where the antiligand employed with both particles is binds to multiple sites, limited incubation of the sample with a low concentration of one of the antiligand conjugated particles followed by addition of an excess of the other antiligand conjugated particle may be employed.

One can further employ another technique, where particular compositions recognize antigen-antibody complexes, but do not significantly bind to antigen or antibody by themselves. Such materials include rheumatoid factor and Clq. In this case, either or both of the particles would be conjugated with a material, the anticomplex, which recognizes the complex. When both particles are conjugated with anticomplex, the particles, the sample, and the mip reciprocal to that in the sample are combined. When one particle is conjugated with anticomplex, the other particle is conjugated with the antigen and both particles would be combined with sample that contains antibodies (receptors) to the antigen.

Where haptens or monoepitopic analytes are involved and bridging is desired, one can provide a molecule having a plurality of the single epitopes covalently bonded to a central hub. By having receptors for the monoepitopic analyte on both of the particles, the analyte present in the sample can be allowed to fill a portion of the available binding sites present on the particles. Upon adding the hub-bound epitopes, the rate and amount of binding between fluorescent particles and quenching particles will be related to the amount of available binding sites remaining on the particles and hence the amount of analyte present in the sample. The same type of system can be employed with antigens, where monoclonal antibodies are employed. To the extent that the antigen has unique determinant sites and the antibodies recognize only one determinant site, in effect one has a monoepitopic analyte.

MATERIALS

The components employed in the assay will be the fluorescent particle conjugate, the opaque particle conjugate, the analyte, and as appropriate other reagents, such as mips, polymips, or the like. Employed in the preparation of the reagents will be particles or beads, mips, or other specific binding members.

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000 more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
proteoglycans
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
  $\alpha_1$-glycoprotein
$\alpha_1\chi$-Glycoprotein
Thyroxin-binding globulin
Inter-$\alpha$-trypsin-inhibitor
Gc-globulin
  (Gc 1-1)
  (Gc 2-1)
  (Gc 2-2)
Haptoglobin
  (Hp 1-1)
  (Hp 2-1)
  (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
  (IgG) or $\gamma$G-globulin
Mol. formula:
  $\gamma_2\kappa_2$ or $\gamma_2\lambda_2$
Immunoglobulin A (IgA)
  or $\alpha$A-globulin
Mol. formula:
  $(\alpha_2\kappa_2)^n$ or $(\alpha_2\lambda_2)^n$
Immunoglobulin M
  (IgM) or $\gamma$M-globulin
Mol. formula:
  $(\mu_2\kappa_2)^5$ or $(\mu_2\lambda_2)^5$
Immunoglobulin D(IgD)
  or $\gamma$D-Globulin ($\gamma$D)
Mol. formula:
  $(\delta_2\kappa_2)$ or $\delta_2\lambda_2)$
Immunoglobulin E (IgE)
  or $\gamma$E-Globulin ($\gamma$E)
Mol. formula:
  $(\epsilon_2\kappa_2)$ or $(\epsilon_2\lambda_2)$
Free $\kappa$ and $\lambda$ light chains
Complement factors:
C'1
  C'1q C'1r
C'1s
C'2
C'3
$\beta_1$A
$\alpha_2$D
C'4
C'5
C'6
C'7
C'8
C'9

Important blood clotting factors include:

| BLOOD CLOTTING FACTORS | |
| --- | --- |
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:
Peptide and Protein Hormones
  Parathyroid hormone
    (parathromone)
  Thyrocalcitonin
  Insulin
  Glucagon
  Relaxin
  Erythropoietin
  Melanotropin
    (melanocyte-stimulating hormone; intermedin)
  Somatotropin
    (growth hormone)
  Corticotropin
    (adrenocorticotropic hormone)
  Thyrotropin
  Follicle-stimulating hormone
  Luteinizing hormone
    (interstitial cell-stimulating hormone)
  Luteomammotropic hormone
    (luteotropin, prolactin)
  Gonadotropin
    (chorionic gonadotropin)
Tissue Hormones
  Secretin
  Gastrin
  Angiotensin I and II
  Bradykinin
  Human placental lactogen
Peptide Hormones from the Neurohypophysis
  Oxytocin
  Vasopressin
  Releasing factors (RF)
    CRF, LRF, TRF, Somatotropin-RF,
    GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
| --- | --- |
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and turberculin |
| Klebsiella aerogenes | Polysaccharide |
| Klebsiella cloacae | Polysaccharide |
| Salmonella typhosa | Lipopolysaccharide, Polysaccharide |
| Salmonella typhimurium; Salmonella derby Salmonella pullorum | Polysaccharide |
| Shigella dysenteriae | Polysaccharide |
| Shigella flexneri | |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction assayed. Microorganisms of interest include:
Corynebacteria
  Corynebacterium diptheriae
Pneumococci
  Diplococcus pneumoniae
Streptococci
  Streptococcus pyogenes
  Streptococcus salivarus
Staphylococci
  Staphylococcus aureus
  Staphylococcus albus
Neisseriae
  Neisseris meningitidis
  Neisseria gonorrheae
Enterobacteriaciae

| Escherichia coli | } The coliform |
| --- | --- |
| Aerobacter aerogenes | |

| Klebsiella pneumoniae | bacteria |
| Salmonella typhosa | |
| Salmonella choleraesuis . | The Salmonellae |
| Salmonella typhimurium | |
| Shigella dysenteriae | |
| Shigella schmitzii | |
| Shigella arabinotarda | |
| Shigella flexneri | The Shigellae |
| Shigella boydii | |
| Shigella Sonnei | |

Other enteric bacilli

| Proteus vulgaris | |
| Proteus mirabilis | Proteus species |
| Proteus morgani | |

Pseudomonas aeruginosa
Alcaligenes faecalis
Vibrio cholerae
Hemophilus-Bordetella group

| Hemophilus influenzae, | H. ducreyi |
| | H. hemophilus |
| | H. aegypticus |
| | H. parainfluenzae |

Bordetella pertussis
Pasteurellae
    Pasteurella pestis
    Pasteurella tulareusis
Brucellae
    Brucella melitensis
    Brucella abortus
    Brucella suis
Aerobic Spore-forming Bacilli
    Bacillus anthracis
    Bacillus subtilis
    Bacillus megaterium
    Bacillus cereus
Anaerobic Spore-forming Bacilli
    Clostridium botulinum
    Clostridium tetani
    Clostridium perfringens
    Clostridium novyi
    Clostridium septicum
    Clostridium histolyticum
    Clostridium tertium
    Clostridium bifermentans
    Clostridium sporogenes
Mycobacteria
    Mycobacterium tuberculosis hominis
    Mycobacterium bovis
    Mycobacterium avium
    Mycobacterium leprae
    Mycobacterium paratuberculosis
Actinomycetes (fungus-like bacteria)
    Actinomyces israelii
    Actinomyces bovis
    Actinomyces naeslundii
    Nocardia asteroides
    Nocardia brasiliensis
The Spirochetes

| Treponema pallidum | Spirillum minus |
| Treponema pertenue | Streptobacillus moniliformis |

Treponema carateum

Borrelia recurrentis
    Leptospira icterohemorrhagiae
    Leptospira canicola
Mycoplasmas
    Mycoplasma pneumoniae
Other pathogens
    Listeria monocytogenes
    Erysipelothrix rhusiopathiae
    Streptobacillus moniliformis
    Donvania granulomatis
    Bartonella bacilliformis
Rickettsiae (bacteria-like parasites)
    Rickettsia prowazekii
    Rickettsia mooseri
    Rickettsia rickettsii
    Rickettsia conori
    Rickettsia australis
    Rickettsia sibiricus
    Rickettsia akari
    Rickettsia tsutsugamushi
    Rickettsia burnetii
    Rickettsia quintana
Chlamydia (unclassifiable parasites bacterial/viral)
    Chlamydia agents (naming uncertain)
Fungi
    Cryptococcus neoformans
    Blastomyces dermatidis
    Histoplasma capsulatum
    Coccidioides immitis
    Paracoccidioides brasiliensis
    Candida albicans
    Aspergillus fumigatus
    Mucor corymbifer (Absidia corymbifera)

| Rhizopus oryzae | |
| Rhizopus arrhizus | Phycomycetes |
| Rhizopus nigricans | |

Sporotrichum schenkii
    Fonsecaea pedrosoi
    Fonsecaea compacta
    Fonsecaea dermatidis
    Cladosporium carrionii
    Phialophora verrucosa
    Aspergillus nidulans
    Madurella mycetomi
    Madurella grisea
    Allescheria boydii
    Phialosphora jeanselmei
    Microsporum gypseum
    Trichophyton mentagrophytes
    Keratinomyces ajelloi
    Microsporum canis
    Trichophyton rubrum
    Microsporum andouini
Viruses
Adenoviruses
Herpes Viruses
    Herpes simplex
    Varicella (Chicken pox)
    Herpes Zoster (Shingles)
    Virus B
    Cytomegalovirus
Pox Viruses
    Variola (smallpox)
    Vaccinia
    Poxvirus bovis Paravaccinia
*Molluscum contagiosum*
Picornaviruses
   Poliovirus
   Coxsackievirus
   Echoviruses
   Rhinoviruses
Myxoviruses
   Influenza (A, B, and C)
   Parainfluenza (1–4)
   Mumps Virus
   Newcastle Disease Virus
   Measles Virus
   Rinderpest Virus
   Canine Distemper Virus
   Respiratory Syncytial virus
   Rubella Virus
Arboviruses
   Eastern Equine Eucephalitis Virus
   Wastern Equine Eucephalitis Virus
   Sindbis Virus
   Chikugunya Virus
   Semliki Forest Virus
   Mayora Virus
   St. Louis Encephalitis Virus
   California Encephalitis Virus
   Colorado Tick Fever Virus
   Yellow Fever Virus
   Dengue Virus
Reoviruses
   Reovirus Types 1–3
Hepatitis
   Hepatitis A Virus
   Hepatitis B Virus
Tumor Viruses
   Rauscher Leukemia Virus
   Gross Virus
   Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Ligand Analog

The ligand analog will differ from the ligand either by replacement of a hydrogen or a functionality with a bond or a linking group which has a functionality for forming a covalent bond to another molecule having an active functionality, such as an hydroxyl, amino, aryl, thio, olefin, etc., where the resulting compound differs from the ligand by more than substitution of a hydrogen by the molecule to which it is conjugated. The linking group will normally have from 1-20 atoms other than hydrogen, which are carbon, oxygen, sulfur, nitrogen, and halogen of atomic number 17-35. The functionalities which are involved include carbonyl, both oxo and non-oxo, active halogen, diazo, mercapto, ethylene, particularly activated ethylene, amino, and the like. The number of heteroatoms will generally range from about 0-6, more usually from about 1-6, and preferably from about 1-4. A description of linking groups may be found in U.S. Pat. No. 3,817,837, which disclosure is incorporated herein by reference.

For the most part, the linking groups will be aliphatic, although with diazo groups, aromatic groups are involved. Generally, the linking group is a divalent chain having about 1-10, more usually from about 1-6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analogous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjunction with diimides, or as mixed anhydrides with carbonate monesters or as active carboxylic esters e.g. N-hydroxy succinimide or p-nitrophenyl. Nitrogen analogs may be employed as imidoesters. Aldehydes can be used to form imines under reductive amination conditions e.g. in the presence of borohydrides, to produce alkylamines. Other non-oxo carbonyl groups which may be employed include isocyanates and isothiocyanates. In addition, active halide may be employed, particularly bromoacetyl groups.

In most instances, the ligand will have one or more functional groups which may be employed as the site for linking the linking group. Particularly, hydroxy, amino and aryl groups, particularly activated aryl groups find use. Also, oximes may be prepared from oxo functionalities and the hydroxyl used as a site for joining to a linking group, such as carboxymethyl.

The choice of linking group will vary widely, depending upon the functionalities which are present in the ligand, in the compound to which the ligand is to be conjugated, the nature and length of the linking group desired, and the like.

Fluorescent Particle

The fluorescent particle is a solid insoluble particle of at least about 50 nm and not more than about 50 microns, usually at least about 100 nm and less than about 25 microns, preferably from about 0.2 to 5 microns diameter. The particle may be organic or inorganic, preferably non-porous with respect to the sample mip or mip complex, preferably of a density approximating water, generally from about 0.7 to about 1.5 g/ml, and composed of material exclusive of the chromophore that is at least partially transparent in the wavelength range absorbed and emitted by the fluorescer, usually transparent in the range of about 300 to 700 nm.

The organic particles will normally be polymers, either addition or condensation polymers, which are readily dispersible in the assay medium. The organic polymers will also be adsorptive or functionalizable so as to bind, either directly or indirectly, the mip or other specific binding member.

The particles can be derived from naturally occurring materials, naturally occurring materials which are synthetically modified and synthetic materials. Among organic polymers of particular interest are polysaccharides, particularly cross-linked polysaccharides, such as agarose, which is available as Sepharose, dextran, available as Sephadex and Sephacyl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like. Inorganic polymers include silicones, glasses, available as Bioglas, and the like. Natural or synthetic assemblies such as liposomes, phospholipid vesicles, and cells can also be employed.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of binding a mip through specific or non-specific non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to the fluorescent particle is well known and is amply illustrated in the literature. See for example Cuatrecasas, J. Biol. Chem. 245 3059 (1970). The length of a linking group to the mip or mip analog may vary widely, depending upon the nature of the compound being linked, the effect of the distance between the compound being linked and the particle on the binding of the mip, and the like. The mip will be substantially bound to the outer surface of the particle.

The fluorescers bound to the particle can be bound in conventional ways. The fluorescers will usually be dissolved in or bound covalently or non-covalently to the particle and will frequently be substantially uniformly bound through the particle.

Fluorescenated latex particles are taught in U.S. Pat. No. 3,853,987 and are available commercially as Covaspheres from Covalent Technology Corp. The particular manner in which the fluorescer is bound to the latex particle is not critical to this invention, so long as the binding provides for substantial fluorescence.

The fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p,p'-diaminobenzophenone imines, anthracenes, oxacarboxyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3- chromen, indole, xanthene, 7-hydroxycoumarin, 4,5-benzimidazoles, phenoxazine, salicylate, strophanthidin, porphyrins, triarylmethanes, flavin and rare earth chelates oxides and salts.

Individual fluorescent compounds which have functionalities for linking or can be modified to incorporate such functionalities include dansyl chloride, fluoresceins such as 3,6-dihydroxy-9-phenylxanthhydrone, rhodamineisothiocyanate, N-phenyl 1-amino-8-sulfonatonaphthalene, N-phenyl 2-amino-6-sulfonatonaphthalene, 4-acetamido-4'-isothiocyanatostilbene-2,2'-disulfonic acid, pyrene-3-sulfonic acid, 2-toluidinonaphthalene-6-sulfonate, N-phenyl, N-methyl 2-amino-naphthalene-6-sulfonate, ethidium bromide, atebrine, auromine-0, 2-(9'-anthroyl)palmitate, dansyl phosphatidylethanolamine, N-(p-2-benzimidazolyl)phenyl)maleimide, 4-phenyl-spiro(furan-2.1'-phthalan)-3-3'-dione, N,N-dioctadecyl oxacarbocyanine, N,N'-dihexyl oxacarbocyanine, merocyanine, 4-(3'-pyrenyl)butyrate, d-3-aminodesoxyequilenin, 12-(9'-anthroyl)stearate, 2-methylanthracene, 9-vinylanthracene, 2,2'-vinylene-p-phenylene)bis-benzoxazole, p-bis[2-(4-methyl-5-phenyl-oxazolyl)]benzene, 6-dimethylamino-1,2-benzophenazin, retinol, bis(3'-aminopyridinium) 1,10-decandiyl diiodide, sulfonaphthyl hydrazone of hellebrigenin, chlortetracycline, N(7-dimethylamino-4-methyl-2-oxo-3-chromenyl)maleimide, N-[p-2-benzimidazoyl)phenyl]-maleimide, N-(4-fluoranthyl)maleimide, bis(homovanillic acid), resazurin, 4-chloro-7-nitro-2.1.3-benzooxadiazole, merocyanine 540, resorufin, rose bengal, 2,4-diphenyl-3(2H)-furanone, methylumbelliferone, 9,10-dibromoanthracene, 9,10-diethinylanthracene, and eosin.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

The chemiluminescent source may have a single component or a plurality of components, usually two or three components. The chemiluminescent source may be divided into two categories: those which do not involve the intermediacy of enzyme catalysis; and those which do involve enzyme catalysis.

Considering chemiluminescent sources which do not involve enzyme catalysis, only those sources can be employed which chemiluminesce under conditions which do not interfere with the other reactions or interactions involved in the assay. While ordinarily, chemiluminescent sources which are dependent on nonaqueous solvents and strong basic conditions, greater than pH11, will not be useful, techniques can be employed involving rapid injections or flow techniques where the modulated emission is substantially completed before the protein is denatured and significant dissociation occurs. After injection of base, one would observe a burst of light, which could be measured.

A diverse number of families of compounds have been found to provide chemiluminescence under a variety of conditions. One family of compounds is 2,3-dihydro-1,4-phthalazinediones. The most popular compound is luminol, which is the 5-amino compound. Other members of the family include the 5-amino-6,7,8-trimethoxy and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents.

The next group of chemiluminescent compounds are indolen-3-yl hydroperoxides, precursors thereto and derivatives thereof.

The next group of compounds is the bis-9,9'-biacridinium salts, of which lucigenin, N,N'-dimethyl-9,9'-biacridinium dinitrate is illustrative. These compounds chemiluminesce upon combination with alkaline hydrogen peroxide.

The next group of compounds is acridinium salts which are substituted in the 9 position. Particular substituents are carboxylic esters, particularly the aryl esters, acyl substituents, particularly benzoyl, and cyano. Alkaline hydrogen peroxide is employed to induce chemiluminescence.

Another group of compounds is various acyl peroxy esters and hydroperoxides, which may be formed in situ, in combination with compounds such as 9,10-diphenylanthracene.

Another source of chemiluminescence is hydroperoxides, e.g. tetralin hydroperoxide, in combination with metal complexes, particularly porphyrins and phthalocyanines, where the metals are iron and zinc.

Preferred systems are those which provide a satisfactory quantum efficiency of emission from the chemiluminescer at a pH at or below 11, preferably at or below 10.

The next group of compounds is based on chemiluminescers which chemiluminesce under enzymatic catalysis. Primarily, there are two groups of enzymatically catalyzed chemiluminescers. The first group is those compounds which chemiluminesce in combination with alkaline hydrogen peroxide. By employing a peroxidase e.g. horse radish peroxidase, in combination with hydrogen peroxide and the chemiluminescer, chemiluminescence can be achieved. Illustrative systems include 2,3-dihydro-1,4-phthalazinediones.

The second enzymatic source of chemiluminescence is based on luciferins and their analogs and luciferases. Of particular importance are bacterial luciferases.

It should be noted that the absorption and emission characteristics of the bound chromogen may differ from the unbound chromogen. Therefore, when referring to the various wavelength ranges and characteristics of the chromogen, it is intended to indicate the chromogens as employed and not the chromogen which is unconjugated and characterized in an arbitrary solvent.

Energy Absorbent or Quenching Particles

The energy absorbent particles will be of a size in the range of about 50 nm to 50 microns, more usually 100 nm to 20 microns, and preferably 200 nm to 5 microns diameter. The energy absorbent particle may be larger, but will normally be less than half, desirably less than one-fifth, and more desirably less than one-tenth times the volume of the light emitting or fluorescent particle. The limitation on the size of the particle is that it should effectively quench the fluorescent particles without rapid settling and it should not create substantial fluctuations in signal due to its movement through the measurement zone of a device for measuring electromagnetic radiation.

The particles may be homogeneous or non-homogeneous, isotropic or anisotropic, in that the particle composition or quenching functionalities may be uniformly or non-uniformly dispersed, usually uniformly dispersed. The particles should provide sufficient quenching, so that at maximum quenching in an assay greater than one percent of the emitted light is absorbed, preferably greater than ten percent, more preferably greater than fifty percent. Absorptivity will be dependent on such factors as size, usually smaller particles being less efficient quenchers than larger particles.

Quenching can be as a result of energy transfer, opacity or a combination of both. With fluorescent particles there may be a substantial diminution of fluorescence when the fluorescent particles are brought into close proximity due to mip binding where the fluorescent particles absorb a significant fraction of the light in the assay medium. Therefore, by appropriate choice of mips for conjugation to the fluorescent particles, the same particle may serve as both the fluorescer and the quencher.

Opaque particles are defined as particles that transmit less than 10% of the light in the wavelength range of interest. For the most part, opaque particles are preferred, particularly particles which absorb substantially the entire visible range.

Quenching particles are employed which may be conjugated, covalently or non-covalently to a specific binding pair member. The quenching particles must be capable of binding to a specific binding pair member or be capable of modification for such binding. The binding may be as a result of adsorption or by means of introduction of functional groups which can form covalent bonds with the mip. The mip will be substantially bound to the surface accessible to the fluorescent particles.

The particles which are employed can be adsorptive or non-adsorptive to proteins; the particles may be naturally occurring, synthetic or combinations thereof, a single material or mixture of materials and are normally chemically inert. The opaque particles absorb light in the wavelength of interest and are frequently black. Illustrative opaque materials include particles of carbon, such as activated charcoal, carbon black, lampblack, graphite and collodial carbon, collodial metal particles, metal oxide particles, metal chalcogenide particles, light absorbing synthetic polymeric particles, e.g. containing one or more chromophoric functionalities, covalently or non-covalently incorporated in the particle, which absorb light in the wavelength range of interest, liposomes e.g. erythrocytes, etc.

The particles are dispersible in the assay medium and should provide a relatively stable disperson or be capable of a relatively stable dispersion by virtue of the addition of a dispersant. It is only necessary that the particles remain dispersed during the period of measurement although longer times are desirable.

While the manner in which the opaque particle represses light emission may vary, one or more of the following factors may be involved wholly or in part: energy acceptance; shielding; light absorption; or perturbation of energy levels through chemical or physical interaction with the particle surface.

Ancillary Materials

Various ancillary materials may be employed in the subject assays. As already indicated, with monoepitopic ligands, protocols may require that a polyligand or poly(ligand analog) be included. In other instances, a mip may be involved, particularly where receptors for antibodies or for ligand-antibody complexes are involved. In addition, sufficient buffering agent may be employed to provide a buffer concentration from about 0.01 to 1M. The amount of buffer which is chosen will be sufficient to control the pH in relation to the sample which is employed. In addition to buffers, other materials may be added. Stabilizers such as proteins, e.g., albumins, in amounts to provide a concentration of up to about 1.5 weight percent; protective compounds, such as bacteriostats or bacteriocides, e.g., sodium azide, in amounts to provide concentrations of up to about 1 weight percent; as well as other materials for specific effects, such as surfactants, chelating agents, oxidation inhibitors, substances to increase the density of the medium such as Percoll ®, cesium chloride, or Hypaque ®, agents to increase viscosity such as glycerol and glucose, and agents to affect binding such as PEG and sodium fluoride.

Kits

As a matter of convenience, the reagents can be provided as kits, where the reagents are in predetermined ratios, so as to substantially optimize the sensitivity of the assay in the range of interest. The fluorescent particle conjugate and opaque particle conjugate may be present in powder form, in a dispersible gel, or as a concentrate in an aqueous medium. By employing high density additives or adjusting the density of the particles, the desired density relationship can be achieved between the aqueous assay medium and the particles.

The reagents provided in the kits will be the fluorescent particle conjugate, the opaque particle conjugate and ancillary reagents as appropriate. Depending upon the particular materials and protocol, the fluorescent particle conjugate and opaque particle conjugate may be combined as a single reagent in conjunction with various other reagents or be present as separate reagents. The particular ratio of the two particles will vary widely depending upon the protocol to be employed, the particular mips involved, as well as the dynamic assay range.

The following examples are offered by way of illustration and not by way of limitation.

EXPERIMENTAL

EXAMPLE 1

Generalized Procedure for Protein Coupling to Fluorescent Beads

Covaspheres MX (Covalent Technology Corp.) are hydrophilic fluorescent micro-sized (0.935 micron diameter) monodispersed polystyrene spheres. They are "activated" and form permanent covalenty bonds to protein by amine and sulfhydryl groups.

In preparing the conjugate, 100 μl of a 1.4% suspension of Covaspheres is added to 1 ml of normal saline containing 50 micrograms of protein with agitation. The sample is incubated for one hour at room temperature, centrifuged for 4 min and the supernatant discarded. The pellet is washed twice by resuspension with PBS-3 buffer pH7.4, centrifuged and then resuspended by sonication in 0.5 ml of the above buffer containing 0.1% ovalbumin. The coupling reaction is essentially complete in one hour and the protein uptake is about 0.025% by weight. The beads may then be refrigerated for future use.

EXAMPLE 2

Antibody Conjugation to Carbon

To 20 mg carbon black, Sterling R, V-5373, 1 mg of rabbit anti-human IgG in 1 ml PBS/NaN$_3$ buffer, pH 7.4 is added. After sonicating the mixture for 1–2 min, the mixture is stirred overnight in the cold. The carbon particles are spun-down and the amount of protein in the supernatant checked by absorption at 280 nm to determine the binding, which is generally in the range of 75 to 95% of the available antibody. The carbon pellet is washed twice with PBS/NaN$_3$/Tween 20 buffer and resuspended in 0.1% ova/PBS/N$_3$T20 buffer, the carbon black being brought down each time by centrifugation.

In order to demonstrate the subject invention, the following experiments were carried out. A series of tubes were prepared by adding in each tube 50 μl of a ⅕th dilution of a carbon particle composition to 1 ml of 0.1% ovalbumin/PBS/NaN$_3$ buffer. A series of solutions of different concentrations of human IgG were prepared which were then diluted with 250 μl of the above buffer and added to he above tubes in duplicate. The assay mixtures were then incubated with rotation at room temperature for 90 min. At the end of the 90 min, 250 μl of the fluorescent beads conjugated to human IgG were added in the above buffer and the assay mixture incubated for an additional 90 min. The fluorescence of the assay mixture was then determined.

The following table indicates the results.

TABLE I

| IgG conc. μg/assay | Fluorescence Arbitrary Units |
|---|---|
| 100 | 601 |
| 10 | 593 |
| 1 | 570 |
| 0.1 | 523 |
| 0.01 | 440 |
| 0.001 | 424 |
| 0.0001 | 408 |
| 0.0 | 399 |

The above results demonstrate that a sensitive assay is available by employing fluorescent beads which are functionalized with a mip in combination with mip functionalized opaque beads, particularly charcoal. Because of the high multiplication of fluorescence from a fluorescent bead, large modulation of signal can be achieved through the interaction of the quencher particle with the fluorescent beads. Thus, great enhancement in signal changes with small changes in analyte concentration and sensitivity to low concentrations of analyte can be obtained. The subject method finds particular application in serological methods, where one is concerned with antibody to a specific antigen. The antigen can be bound to the fluorescent particle. Only the complementary mip will bind to the antigen bound to the fluorescenated particle, leaving a large amount of unbound nonspecific antibodies in the medium. The quencher particle can also be bound to antigen or to anti-human immunoglobulin or other materials which are specific for antibodies, either by themselves or in a particular conformation, e.g. rheumatoid factor, for a plurality of antibodies in close proximity. Despite the large amount of immunoglobulin in a serum sample, employing an excess of functionalized quencher particle, will permit a sufficient amount of the functionalized quencher particle to bind to the fluorescent particles to provide for substantial modulation of the fluorescence signal in the presence of antibodies to the specific antigen. This method has substantial advantages because of the presence of only a small amount of the antibody of interest as compared to the total amount of immunoglobulin present in the serum sample.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of an analyte in a sample suspected of containing said analyte, wherein said analyte is a member of a specific binding pair-mip-, said method comprising the steps of:

in an aqueous assay medium, combining (1) said analyte, (2) a mip-bound-light emitting particle which is a water insoluble particle of at least 50 nm in diameter capable of light emission upon activation having functionalities capable of light emission distributed within said particle and a plurality of mips bound to said particle, and (3) a mip-bound-quencher particle which is a quencher particle of at least 50 nm in diameter to which a plurality of mips are bound to provide a mip-bound-quencher particle, wherein when said mip-bound-quencher particle is bound to said mip-bound-light emitting particle through a mip bridge, there is substantial reduction in light emission of said mip-bound-light emitting particle, and wherein said mips of said analyte, mip-bound-light emitting particle and mip-bound-quencher particle include at least one complementary pair, and wherein the formation of said mip bridge is modulated by said analyte, and wherein the amount of mip-bound-quencher particle which becomes bound to said mip-bound-light emitting particle is related to the amount of analyte in said medium; and determining the amount of light emission in said medium as compared to an assay medium having a known amount of analyte.

2. A method according to claim 1, wherein said quencher particle is charcoal.

3. A method according to claim 2, wherein said charcoal particle is of from 50 nm to 50 microns in diameter.

4. A method according to claim 1, wherein said light emitting particle is an addition polymer fluorescent particle.

5. A method according to claim 1, wherein said mip of said mip-bound-light emitting particle and said analyte form one complementary pair and said mip of said mip-bound-quencher particle and said analyte form the same complementary pair.

6. A method according to claim 1, wherein said mip of said mip-bound-light emitting particle and said analyte form one complementary pair and said mip of said mip-bound-quencher particle and said analyte form a second complementary pair.

7. A method according to claim 1, wherein said analyte is a protein.

8. A method according to claim 7, wherein said protein is gamma-globulin.

9. A method according to claim 7, wherein said protein is albumin.

10. A method according to claim 1, wherein said light emitting particle is a fluorescent particle which absorbs light of wavelength greater than about 350 nm and emits light of wavelength greater than about 400 nm and is different from said quencher particle.

11. A method for determining the presence of an analyte in a sample suspected of containing said analyte, wherein said analyte is a member of a specific binding pair-mip-, said method comprising the steps of:

in an aqueous assay medium, combining (1) said analyte, (2) a mip-bound-fluorescent particle which is a fluorescent water insoluble particle of a size in the range of about 100 nm to 20μ in diameter and having fluorescent functionalities substantially uniformly distributed within said particle and a plurality of mips bound to said particle and (3) a mip-bound-quencher particle which is a carbon quencher particle to which a plurality of mips are bound to provide a mip-bound-quencher particle, wherein when said mip-bound-quencher particle is bound to said mip-bound-fluorescent particle through a mip bridge, there is substantial reduction of fluorescence of said mip-bound-fluorescent particle, and wherein said mips of said analyte, mip-bound-fluorescent particle and mip-bound-quencher particle include at least one complementary pair, and wherein the formation of said mip bridge is modulated by said analyte, and wherein the amount of mip-bound-quencher particle which becomes bound to said mip-bound-fluorescent particle is related to the amount of analyte in said medium; and determining the amount of fluorescence in said medium as compared to any assay medium having a known amount of analyte.

12. A method according to claim 11, wherein said carbon quenching particle is a charcoal particle of up to about 50μ in diameter and less than about half the size of said mip-bound-fluorescent particle.

13. A method according to claim 11, wherein said mip-bound-fluorescent particle is of a size in the range of about 200 nm to 5μ diameter and said carbon quenching particle is of less than half the size of said fluorescent particle.

14. A method for determining the presence of an analyte in a sample suspected of containing said analyte wherein said analyte is a member of a specific binding pair-mip-, said method comprising the steps of:

in an aqueous assay medium, combining said analyte and mip-bound-fluorescer particles which are fluorescent water insoluble particles of a size in the range of about 100 nm to 20μ in diameter having fluorescent functionalities substantially uniformly distributed within each of said particles and a plurality of mips bound to each of said particles wherein, when two or more of said mip-bound-fluorescent particles are brought together through mip bridges by binding to analyte or as a result of having complementary mips on mip-bound-fluorescent particles, there is a substantial diminution in fluorescence, and wherein said mips of said analyte and mip-bound-fluorescent particles include at least one complementary pair, and wherein the formation of said mip bridge is modulated by said analyte, and wherein the amount of mip-bound-fluorescer particles which are brought into close proximity by mip bridges is related to the amount of analyte in said medium; and determining the amount of fluoresence in said medium as compared to an assay medium having a known amount of analyte.

* * * * *